(12) United States Patent
Huisma et al.

(10) Patent No.: US 10,463,024 B2
(45) Date of Patent: Nov. 5, 2019

(54) HIGHLY AUTOMATED SYSTEM AND METHOD OF USING THE SAME TO MEASURE, MONITOR, MANAGE AND CONTROL GRAZING ENVIRONMENT AND ANIMALS

(71) Applicants: Camiel Huisma, Airdrie (CA); Alison Sunstrum, Airdrie (CA)

(72) Inventors: Camiel Huisma, Airdrie (CA); Alison Sunstrum, Airdrie (CA)

(73) Assignee: GROWSAFE SYSTEMS LTD., Alberta (CA)

( * ) Notice: Subject to any disclaimer, the term of this patent is extended or adjusted under 35 U.S.C. 154(b) by 455 days.

(21) Appl. No.: 15/398,850

(22) Filed: Jan. 5, 2017

(65) Prior Publication Data

US 2017/0196203 A1     Jul. 13, 2017

Related U.S. Application Data

(60) Provisional application No. 62/278,096, filed on Jan. 13, 2016.

(51) Int. Cl.
*A01K 29/00*     (2006.01)
*G06Q 30/02*     (2012.01)
(Continued)

(52) U.S. Cl.
CPC .............. *A01K 29/005* (2013.01); *A01K 5/02* (2013.01); *A01K 13/003* (2013.01);
(Continued)

(58) Field of Classification Search
CPC .... A01K 11/006; A01K 29/005; A01K 29/00; A01K 1/12; A01K 11/00; A01K 1/0209;
(Continued)

(56) References Cited

U.S. PATENT DOCUMENTS 5,309,864 A * 5/1994 Harmsen .............. A01K 5/0266
                                                                  119/51.02
5,711,246 A * 1/1998 Yano .................... A01K 11/006
                                                                  119/51.02
(Continued)

FOREIGN PATENT DOCUMENTS

WO     2015/041548 A1     3/2015

OTHER PUBLICATIONS

International Search Report issued in corresponding International Patent Application No. PCT/IB2017/000127 dated Apr. 13, 2017.
(Continued)

*Primary Examiner* — Yvonne R Abbott-Lewis
(74) *Attorney, Agent, or Firm* — Davis & Bujold PLLC; Michael J. Bujold

(57) ABSTRACT

A highly automated system to identify, measure, manage and control individual animals in grazing environments to monitor, analyze, model, predict, promote, optimize, and mitigate a variety of conditions and interactions relating to the grazing environment and an animal's health, welfare, performance, productivity, efficiency, quality, economic and genetic value. The system having a transmitters that identify individual animals. A weighing device that weighs the animal while the animal consumes substances and a dispensing device that controls substance provision to individual animals. A computer considers a number of factors in generating control signals sent to the system to dispense a prescribed amount of mineral, vitamin, medicinal or supplement compound to an individual animal. The system models, predicts and estimates a number of conditions related to the animal and its grazing environment that improve animal welfare, increases production, and preserves and conserves resources.

21 Claims, 4 Drawing Sheets

(51) Int. Cl.
*G06Q 50/02* (2012.01)
*A01K 13/00* (2006.01)
*A01K 5/02* (2006.01)
*G08C 17/02* (2006.01)

(52) U.S. Cl.
CPC ......... *G06Q 30/0278* (2013.01); *G06Q 50/02* (2013.01); *G08C 17/02* (2013.01)

(58) Field of Classification Search
CPC ........ A01K 1/0613; A01K 1/105; A01K 5/02; A01K 5/0216; A01K 5/0266; A01K 5/0275; G06Q 10/087; G06Q 10/08; G06Q 10/063; G06Q 10/06315; G06Q 10/0833; G06Q 50/02
USPC ...... 119/51.02, 174, 14.03, 51.01, 57.6, 712, 119/719, 720, 840, 842, 858, 908; 340/573.3
See application file for complete search history.

(56) References Cited

U.S. PATENT DOCUMENTS

| | | | | |
|---|---|---|---|---|
| 6,651,585 B2* | 11/2003 | van den Berg | .......... | A01K 1/12 119/51.02 |
| 6,868,804 B1* | 3/2005 | Huisma | ................ | A01K 11/006 119/51.02 |
| 6,997,140 B2* | 2/2006 | Finlayson | ............. | A01K 11/00 119/840 |
| 7,296,536 B2* | 11/2007 | Umegard | .................. | A01K 1/12 119/14.03 |
| 7,370,606 B2* | 5/2008 | van der Lely | .......... | A01K 29/00 119/51.01 |
| 8,019,633 B2* | 9/2011 | Stroman | ............... | G06Q 10/063 705/7.11 |
| 8,037,846 B2* | 10/2011 | Pratt | ....................... | A01K 29/00 119/174 |
| 8,282,557 B2* | 10/2012 | Haynes | .................... | A61B 8/08 119/174 |
| 9,167,800 B2* | 10/2015 | Spicola, Jr. | ............ | A01K 29/005 |
| 9,247,719 B1* | 2/2016 | Bennett | .............. | A01K 39/0206 |
| 10,085,419 B2* | 10/2018 | Zimmerman | ......... | A01K 5/0107 |
| 10,127,747 B2* | 11/2018 | Spittle | .................. | G06Q 20/105 |
| 2010/0030036 A1* | 2/2010 | Mottram | ................ | A01K 11/00 600/301 |
| 2011/0298619 A1* | 12/2011 | O'Hare | ................ | A01K 11/008 340/573.1 |
| 2013/0192526 A1 | 8/2013 | Mainini | | |
| 2018/0132519 A1* | 5/2018 | Solly | ...................... | G06Q 10/10 |

OTHER PUBLICATIONS

Supplementary European Search Report corresponsding to EP 17 73 8249 dated Jun. 21, 2019.

* cited by examiner

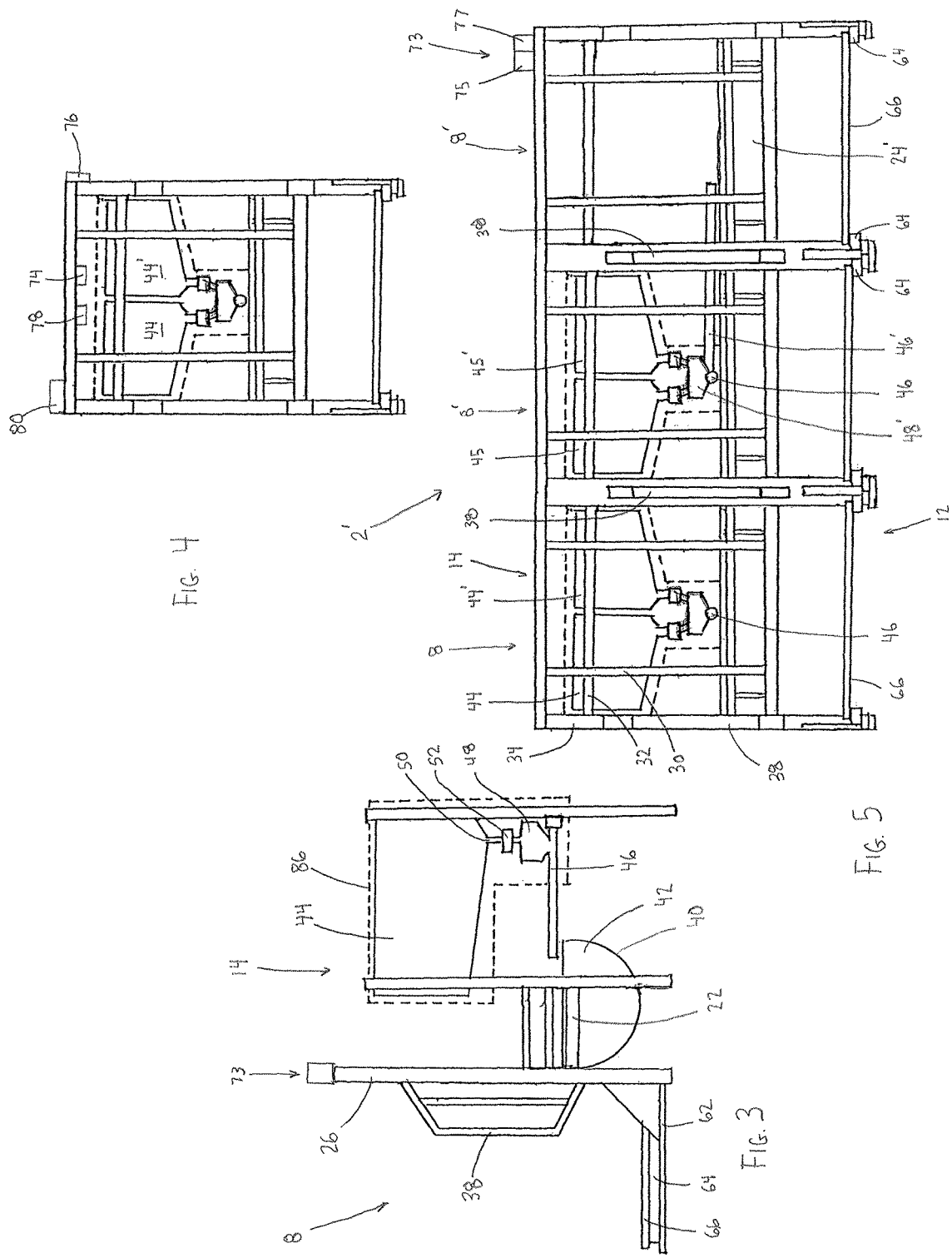

HIGHLY AUTOMATED SYSTEM AND METHOD OF USING THE SAME TO MEASURE, MONITOR, MANAGE AND CONTROL GRAZING ENVIRONMENT AND ANIMALS

FIELD OF THE INVENTION

The present invention relates to an animal identification, measurement, monitoring, management and control system and a method of using the same in grazing animal production environments, and more specifically a system which is capable of being used with multiple transmitters to monitor automatically and continuously the consumption, behavior, and growth of individual animals and their grazing environment in order to measure and predict animal performance; estimate forage and plant disappearance, estimate greenhouse gas emissions, manage pasture and grazing locations, determine the health and reproductive status of individual animals, and respond to conditions monitored through the dispensing of controlled substances which may include minerals, trace minerals, and other supplemental medicinal, pharmaceutical or pest control formulas which promote animal health, growth and welfare and reduce animal stress and environmental impact.

BACKGROUND OF THE INVENTION

Radio Frequency Identification

Radio frequency identification systems have been frequently used to automatically identify objects. One example of a practical application of this technology has resulted in electronic identification of individual animals. The basic elements of such systems include a reader/transmitter, an antenna and a transponder which is attached to an individual animal. The reader/transmitter sends an electromagnetic wave through the antenna to the transponder, which uses this energy to transmit a radio frequency signal back through the antenna to the reader/transmitter. Typically, the signal includes an identification code unique to each transponder. In order to monitor the activities of large herds or groupings of animals, one must be able to monitor multiple transponders. With currently available technology, it is extremely difficult to read multiple transponders using one reader/transmitter.

If each one of the multiple transponders uses the same frequency to transmit its unique identification code back to the reader/transmitter, a single reader/transmitter is unable to readily decipher each individual identification code. In order to make systems with multiple transponders operational, multiple reader/transmitters are required which, in turn, render such systems costly, and will also reduce the area in which the transponders can be simultaneously read.

Measuring Feed Intake—Previous Generation Feed Intake Measurement

A rudimentary way to measure individual feed or water intake has been to house animals individually and record consumption amounts by measuring and manually recording the feed supplied minus the feed refused or remaining. This method is both labor intensive and cost prohibitive. Studies of both swine and cattle have demonstrated that individually housed animals alter their performance significantly from those fed in production environments.

The first generation of electronic feeders acted on the same principle as manual recording. These systems isolate one animal to an individual feeding gate or stall. When the animal enters the stall, the starting trough weight is recorded and, when the animal leaves, the end trough weight is recorded. The difference between starting weight and end weight is determined to be equal the feed intake. Although a gross measurement of what feed disappeared during the time the animal entered and left the feeding stall, this measurement does not take into account what precisely happened during the time period.

The methodology is further compromised when the access to the trough is open at all times and RFID is utilized to identify the animal. RFID is position sensitive and, therefore, might require a variable amount of time to read, compromising the start of the event. Other issues complicating the use of RFID, particularly when measuring visitation by an individual animal to a trough is that the RFID reading field often extends to one or more adjacent trough areas. It is therefore possible when the animal has its head close to one side or the other of a feeding trough that the adjacent RFID antenna also reads the adjacent animal's RFID tag and this potentially creates reading/calculation problems.

These first generation systems typically must be housed in barns providing protection from wind and other environmental conditions adding significantly to the cost of measurement. On a windy day for example, the wind or air pressure applied to the trough often varies by 10N. Such pressure variation becomes very problematic when trying to weigh a typical feed intake meal event normally about 800 grams.

It is to be appreciated that little to no behavioral information is acquired by these first generation systems. Inter-meal activity is not recorded. The effect of animal competition, on intake feeding behavior, is not adequately measured and feeding rates are normally considered to be constant during a feeding event. In terms of behavioral measurement, perhaps the most limiting factor is that the equipment determines what a feeding event or meal event is, by virtue of an animal visit being recorded by the equipment.

An other issue, arising from the use of such equipment, is that typical feeding behaviors are severely modified by the design of the measurement device itself. The animal may only be allowed to visit its specific feed stall to record consumption. Or when two animals wish to enter the trough at the same time, none of the animals will gain access. To overcome the limitations of the system to read multiple tags in close proximity, the system prevents access to feed.

Several of these early generation systems did not include a method to account for feed appearing in the trough. Some tried to properly account for feed appearing by using deflectors that kept animals from the bunks when troughs were being filled. Animals were refused entrance when feed resupplying occurred.

The first generation systems did not include the ability to audit or assess the accuracy of measurements. Several researchers have developed generalized and average statistical assumptions to overcome errors occurring in the first generation systems. In scientific literature, incorrect data is usually adjusted per visit. (e.g., De Haer et al., 1992). Some studies correct for measurement error by estimating individual feed intake of animals and tolerance factors based on those taken in group feeding studies. This circular reasoning does not improve measurement accuracy though data may fit what the researcher perceives to be true based on prior research in group settings.

Background to Feeding Behavior Measurement

In the early 1990s GrowSafe Systems Ltd, ("GrowSafe") developed a computerized data acquisition system that could electronically identify and monitor ostrich chicks. Chicks would visit the feeder about 500 times per day. When chicks became ill, feeding behavior visitation dropped rapidly, declining to about 50 visits per day. This decline in visitations could be trended over a very short time interval, usually within about 4-12 hours. In response to GrowSafe data triggers, avian specialists developed responsive treatment protocols. Using the GrowSafe technology and responsive animal health treatment protocols incorporated therein, the survival rate of the subjects tested improved from 8% to more than 90% (Huisma anecdotal 1993).

Early findings in cattle research, using GrowSafe technology, indicated similar early predictive abilities using animal behavior to identify illnesses at an earlier point in time than otherwise possible. From 1993 to 2000 a significant body of work was compiled by researchers using first generation GrowSafe behavior research technology indicating that feeding behavior patterns, of morbid and non-morbid calves, differ and could be measured (Basarab, 1996); and that the technology had the potential to identify morbid animals before any overt disease symptoms could be detected (Quimby 1999). Research determined that the economic value of morbid calves could be as much as US$0.19 to $0.35 less per kg than for healthy calves (Sowell 1999).

The technological transition from a GrowSafe system that could measure a small bird confined in a controlled environment to a large animal in the cattle environment was extremely complex and required the adaptation and development of new electronics, wireless communication methods, and data acquisition and analysis techniques. Many of these methods are currently protected by patents issued or assigned to GrowSafe Systems Ltd.

Feeding Behavior and Sickness Identification

Researchers have traditionally viewed behavioral changes as simple signs of the debilitative effects of disease. (Weary 2009). Results from several key studies now indicate (1) sickness behavior is a motivational state; (2) sickness behavior is a well-organized adaptive response to infection; (3) cytokines produced by activated leukocytes induce sickness behavior; and (4) cytokines transmit messages from the periphery to the brain using humoral and neural pathways (Johnson 2002). Over the past decade, a substantial shift in thinking about behavioral concepts relating to animal health has occurred.

Identifying sick animals, early in the course of the disease, can be one of the toughest jobs in livestock production. When treated early, most animals have an excellent chance at survival but if an animal is sick for even a few days, treatment regimens are less likely to be effective. The recognition in declines of feed intake can assist with the identification of sick animals. In recent years there has been an increased interest in behavioral indicators of disease. A decrease or change in feeding patterns are usually symptoms of sick individuals. Research has demonstrated decreases in the carcass value of sick animals between animals that have not been treated and those that have been treated once, twice and three times respectively (Schneider 2009). The value of rapid diagnosis and treatment of disease increases when cattle are sold on carcass merit basis because of the negative effects of disease on carcass traits (Larson 2005).

Several epidemiological studies have indicated that even with increased pharmaceutical use, the incidence of morbidity and mortality in feedyards has increased. Total feedlot deaths in 2003 increased by 69% when compared to those in 1994. Bovine Respiratory Disease (BRD) deaths more than doubled (118%) during same time period (Loneragan 2008).

Research indicates that the timing of initial BRD treatment is associated with performance and health outcomes (Babcock 2009) The effectiveness of antimicrobials in the treatment of BRD depends primarily on early recognition and treatment (Apley 2007 Cusack 2003). BRD manifests its economic losses cumulatively, through the cost of treatment, the cost of lost production, and loss due to death, thus emphasizing the importance of prevention and treatment of BRD as early as possible.

Feed Efficiency

For many years, genetic selection programs have focused on production (output) traits, with little attention given to production costs (inputs). Recently, this view has begun to change, and the efficiency of conversion of feed (i.e., the amount of product per unit of feed input) has been recognized as more important.

Within any beef cattle operation, feed costs are undoubtedly the main concern since they typically account for about 60-65% of the total costs of production. Because of the large costs associated with feed, increasing the efficiency of feed has been targeted as a means of improving the profitability of the beef industry. One estimate of feed efficiency is the feed conversion ratio. Traditionally, this was expressed as a feed:gain ratio, but this led to the confusing result that a higher ratio meant a lower efficiency. Today, to overcome this problem, the feed conversions are often expressed as a gain:feed ratio. Even so, results can be misleading, because these ratios are closely correlated to the intake and rate of gain of the animal (Carstens et al., 2004).

Two animals might have a similar gain:feed ratio and still be very different in their feed intakes and rates of gain. Conversely, the same animal at different intakes would certainly have different gain:feed ratios, even though the genetics of the animal had not changed. Therefore, gain:feed ratios have never been widely recognized as a criterion for genetic selection. Residual feed intake (RFI), defined as actual feed intake minus the expected feed intake of each animal, was first proposed as an alternate measure of feed efficiency by Koch et al. (1963). It can be defined, in other words, as the difference between actual feed intake and the expected feed requirements for maintenance of body weight and for weight gain. In contrast to gain:feed, residual feed intake is independent of growth and maturity patterns. Therefore, RFI should be a more sensitive and precise measurement of feed utilization, since it is based on energy intake and energy requirements.

RFI is an individual animal record, taking into account feeding trials. Accurate measurements of daily feed consumed must be made as well as average daily gain. Research has found that there is considerable variation in individual animal feed intakes, both above and below that which is expected or predicted on the basis of size and growth. These findings, along with the fact that individual animals of the same body weight require rather widely differing amounts of feed for the same level of production establishes the scientific base for measuring RFI in beef cattle. (Sainz et al, 2004).

Manure and GHG Emission Reduction

Relative to high RFI cattle, low RFI cattle have been shown to emit less methane—a potent greenhouse gas (GHG). Scientific evidence indicates that a reduction in methane and manure production can be achieved by with a low RFI that is through the reduction in feed intake (Arthur 2009).

Animal Welfare

Animal welfare is a complex issue that includes important scientific, economic and ethical considerations. This issue has the potential of impacting profitability across the entire meat and dairy chain if the end result of animal welfare initiatives requires the adoption of different farming practices or processing methods.

Early identification of sickness, reduction of farm yard stress, animal behavioral measurement and an ability to monitor the welfare and mitigate adverse conditions, for individual animals, is an important animal welfare and research priority.

Antimicrobial Resistance

Current legislation was introduced in March 2009 in the U.S. House of Representatives to prevent the use of antibiotics, important to human health, from being used non-therapeutically in animals. In North America, a ban on the use of antimicrobials for prophylaxis would result in a further increase in the incidence of clinical disease, decreased performance and increased costs of production. The beef cattle feedlot industry has not explored cost-effective feeding and production alternatives to the use of antimicrobials for disease prevention.

It is likely that in response to animal welfare and consumer demand that pharmaceutical products will be targeted to individuals requiring treatment.

SUMMARY OF THE INVENTION

Wherefore, it is an object of the present invention to overcome the above mentioned shortcomings and drawbacks associated with the prior art.

Another object of the present invention is to provide a highly automated system and a method of using the same to models predict and estimate a number of conditions related to an animal and its grazing environment that improve animal welfare, increases production, and preserves and conserves resources.

Another object of the present invention is to implement beneficial land use and grazing management techniques which balance forage maintenance and animal production. Such management techniques ensure proper recovery periods for regrowth of forage which benefits both the animals and grazing-land. Along with enhancing recovery periods, overgrazing of the pastures can be prevented or at least minimized.

A further object of the present invention is to provide a highly automated system having multiple transmitters which automatically and continuously monitor the consumption, behavior, and growth of individual animals and their grazing environment in order to measure and predict animal performance. The highly automated system estimates forage and plant disappearance, greenhouse gas emissions, manages pasture and grazing locations, determines the health and reproductive status of individual animals, and responds to conditions of the animal by adjusting the amount and formulation of the dispensing of controlled substances which may include minerals, trace minerals, and other supplemental medicinal, pharmaceutical or pest control formulas which promote animal health, growth and welfare and reduce animal stress and environmental impact.

Yet another object of the present invention is to provide a highly automated system for monitoring and managing individual animals in a grazing production environment and which comprises transmitters that identify individual animals, measurement units which receive transmitter signals, weight the identified animal and supplies particular substances to the identified animal. A microprocessor in communicates, manages and transmits signals from devices associated with the measurement units. A communication device which receives and transmits signals from the measurement units to local and/or remote computers. The local an/or remote computers receive the signals, and collect measurements from other devices and uses statistical methods, mathematical formulas, and algorithms to estimate, calculate, predict, monitor, evaluate, store and reevaluate animal, plant, soil, environment, operation and industry values, metrics, parameters and interactions. Based on the estimations, calculations and predictions made, the local an/or remote computers determine and transmit appropriate control signals to the different devices of the highly automated system. For example, the local an/or remote computers can send an appropriate control signal to a consumption dispensing station so as to control the amount and/or formulation of supplement provided to the specifically identified animal currently located at the measurement unit.

BRIEF DESCRIPTION OF THE DRAWINGS

The invention will now be described, by way of example, with reference to the accompanying drawings in which:

FIG. 3 is a side view of a measurement unit in accordance with the teachings of the present invention;

FIG. 4 is a front view of a single measurement unit in accordance with the teachings of the present invention;

FIG. 5 is a front view of the system having more than one measurement unit in accordance with the teachings of the present invention.

DETAILED DESCRIPTION OF THE PREFERRED EMBODIMENTS

The present invention will be understood by reference to the following detailed description, which should be read in conjunction with the appended drawings. It is to be appreciated that the following detailed description of various embodiments is by way of example only and is not meant to limit, in any way, the scope of the present invention.

Figure 1:
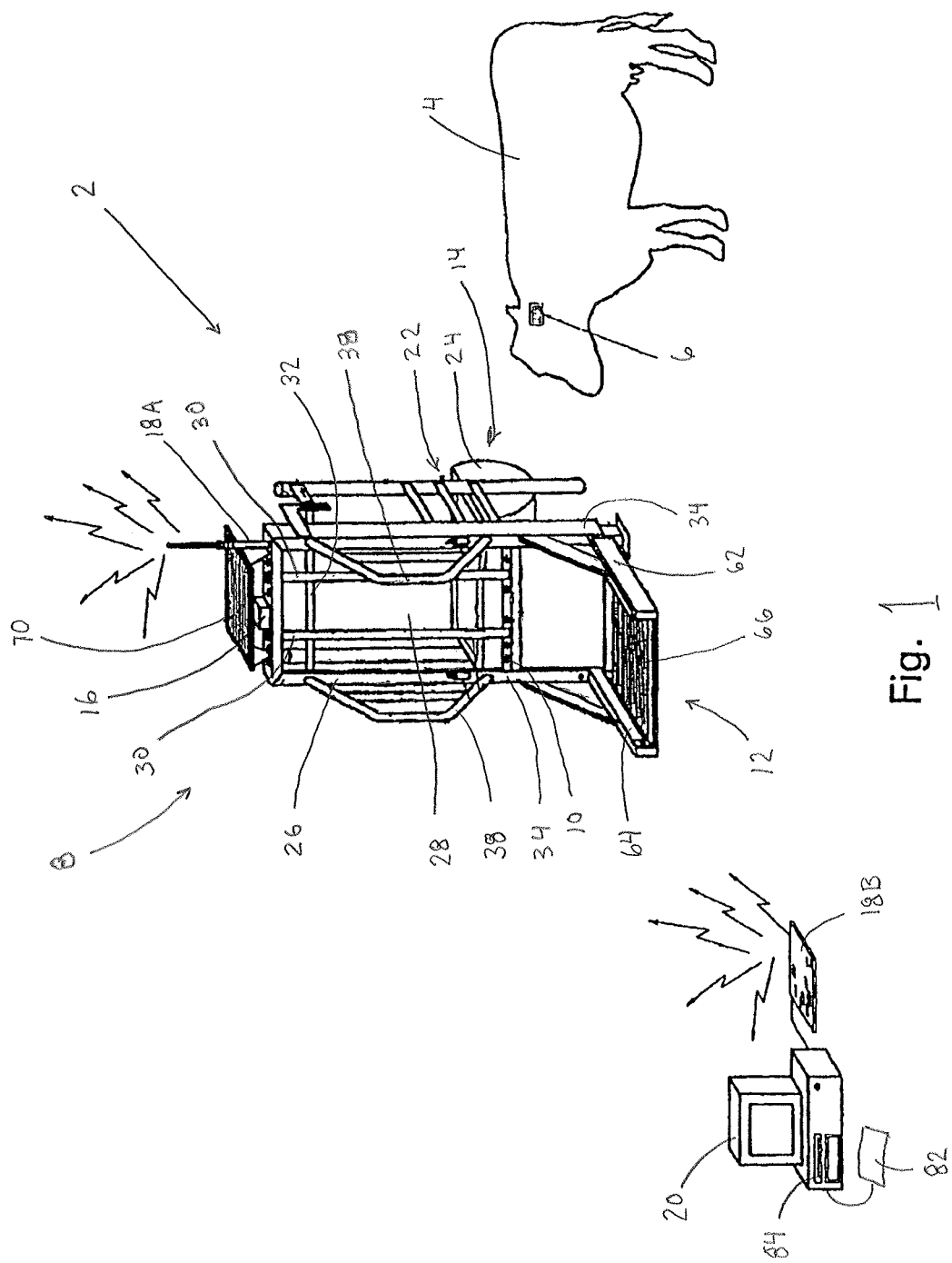
FIG. 1 is a perspective view of the system where one measurement unit identifies, measures, monitors, manages and controls a grazing environment and an animal in accordance with the teachings of the present invention.

Turning now to FIGS. 1 and 4, a general description concerning the various components of the present invention will now be briefly discussed. By way of a general description, the highly automated system 2 to measure, monitor, manage and control animals 4 and a grazing environment and includes a plurality of radio frequency identification (RFID) transmitters 6 and a measurement unit 8 having a receiving device 10, a weighing device 12 and a consumption dispensing station 14. The highly automated system 2 further includes a micro-processor 16, a communication device 18A, 18B and a central computer 20.

Generally the receiving device 10 receives a unique signal from an RFID transmitter 6 when the same is located relatively close to the measurement unit 8, i.e., the receiving device 10 of the measurement unit 8. The receiving device 10 transmits the unique signal to the micro-processor 14 which receives and processes the unique signal prior to transmitting the unique signal, via the communication device 16A, 16B, to the central computer 18 for further processing. The weighing device 12 of the measurement unit 8 measures the partial body weight of the animals 4 carrying the RFID transmitter 6 and transmits the partial body weight measurement to the micro-processor 16 which receives and processes the partial body weight measurement prior to transmitting the same, via the communication device 16A, 16B, to the central computer 20 for further processing. The central computer 20 receives the unique signal and partial body weight measurement and collects further measurements and data from other devices and analyzes these to determine appropriate control signals. The central computer 20 then transmits the control signals, via the communication device 16A, 16B, to the micro-processor 16 which in turn conveys control signals at least to the consumption dispensing station 14. Based on the control signals received, the consumption dispensing station 14 dispenses an amount of consumables to the animal 4 carrying the RFID transmitter 6. The amount of consumables dispensed varies depending on the determined control signals transmitted by the central computer 20 to the consumption dispensing station 14. In this manner, the highly automated system 2 can be utilized to identify, measure, manage and control the consumption behavior, substance intake, weight and growth, reproduction movement and harvest of individual animals 4 in grazing environments based on a number of considerations.

As shown in FIG. 1, the measurement unit 8 comprises a base frame 22 which supports the consumption dispensing station 14 and to which the weighing device 12 is connected. A trough 24 and front panel 26 are supported by the base frame 22 such that the front panel 26 generally separates the trough 24 of the consumption dispensing station 14 from the corresponding weighing device 12 so as to limit access to the trough 24 such that only one animal 4, at a time, is able to extend its head through an opening 28 in the front panel 26 and consume the consumables from the trough 14.

As is conventional in the art, the opening 28 in the front panel 26 is defined by a pair of spaced apart vertical neck bars 30 and a pair of spaced apart horizontal neck bars 32 that are both spaced apart from one another by a sufficient distance so as to permit a single animals 4 to extend its head through the opening 28 in the front panel 26 and access the consumables in the trough 24. To further ensure that only one animal 4 at a time can access the trough 24 of the consumption dispensing station 14, edge support posts 34 form lateral sides of the front panel 26 and, respectively, support a neck guide 38. The neck guides 38 are fixed to the edge support posts 36 and extend from the front panel 26 in a direction opposite the consumption dispensing station 14. The neck guides 38 assist in preventing access of more than one animals 4 at a time to the trough 24. Preferably the positions of at least one of the horizontal and/or vertical neck bars 30, 32 is adjustable so as to permit alteration of the size of the opening 28 in the front panel 26 through which an animals 4 can insert its head to access and consume the consumables in the trough 24. Although the size of the opening 26 should be limited to allow access to the trough 24 by only one animals 4 at a time, the opening 26 should also be large enough to provide the animals 4 sufficient access to generally all of the consumables contained within the trough 24.

As used herein the term "consumables" relates to any substance that can be consumed or ingested by the animals located within the grazing environment including controlled substances such as vitamins, nutrients, minerals, trace minerals, growth promoting substances, supplemental medicinal, pharmaceutical or pest control formulas which promote animals health, growth and welfare and reduce animals stress and environmental impact.

The front panel 26 is formed as a front side of the base frame 22 which is sized to support one trough 24 or a plurality of sequentially arranged troughs 24 (FIG. 2) as discussed below. The interior of the trough 24 is generally defined by a curved wall 40 and a pair of opposed side walls 42. However the trough 24 however can be formed by a front wall and an opposed rear wall and a pair of opposed side walls. The trough 24 is sized to hold a desired volume of consumables, for example, if the consumables to be provided to the animals 4 have a low volume, then the trough 24 may be relatively small in size so as to accommodate, for example, up to a deciliter or decagram of the consumables. However, if the consumables to be provided to the animals 4 have a large volume, the trough 24 may be relatively large in size to contain as much as a decaliter or kilograms of the consumables. It is to be appreciated that the size of the trough 24 is generally not critical as long as the trough 24 is sufficiently sized to contain the desired amount of consumables being provided to the animal 4.

Figure 6:
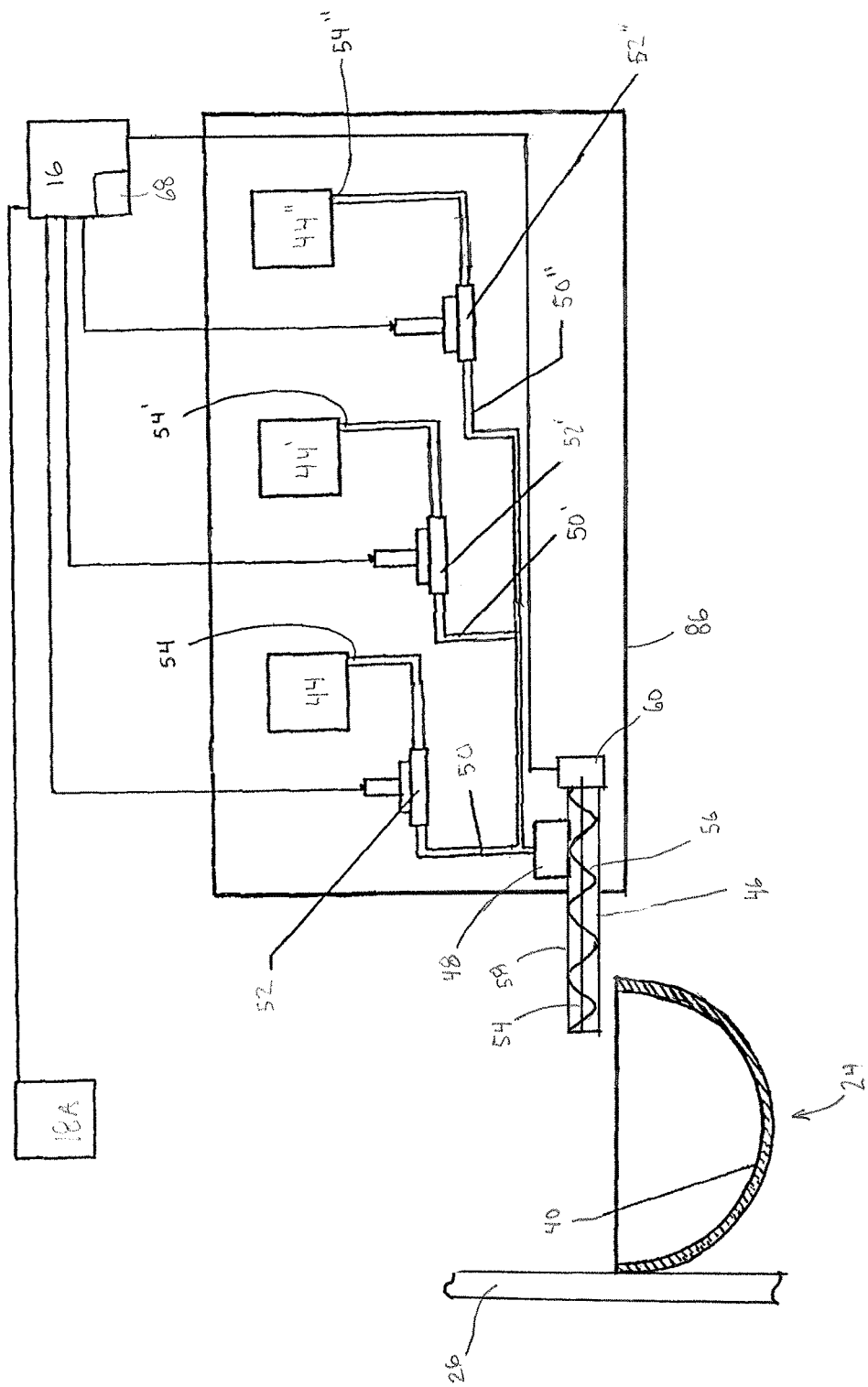
FIG. 6 is diagrammatic view of a consumption dispensing station in accordance with the teachings of the present invention.

As shown in FIGS. 3, 4 and 6, the consumption dispensing station 14 of the measurement unit 8 further comprises one or more containers 44, hoppers, tanks and/or reservoirs (all of which are herein referred to as "containers") which accommodate a supply of one or more different types of consumables. The containers 44 are supported by the base frame 22 and are located relatively closely adjacent the trough 24 such that the consumables accommodated within the containers 44 can be quickly conveyed to the interior of the trough 24 by way of a conveyance device 46. A mixing chamber 48 may be located, with respect to a path of conveyance, between a plurality of containers 44 and the conveyance device 46 to enable the mixing of different consumables so as to customize the formulation of the consumables being conveyed to the trough 24, that is to say the mixing chamber 48 facilitates combining, if desired or deemed necessary, one or more desired controlled substances such as vitamins, nutrients, minerals, trace minerals, growth promoting substances, supplemental medicinal, pharmaceutical or pest control formulas in differing amounts. It is noted that the consumption dispensing stations 14 are not shown in the measurement units 8 illustrated in FIGS. 1 and 2 for the sake of clarity. However it is to be understood that the embodiments of the highly automated systems of FIGS. 1 and 2 comprise consumption dispensing stations 14 as shown in FIGS. 3-5.

As shown in FIG. 6 three containers 44, 44', 44" arranged within a housing 86 are shown connected to the single mixing chamber 48, via different supply conduits 50, 50', 50". Each one of the supply conduits 50, 50', 50" has a solenoid 52, 52', 52" that is associated therewith and located adjacent an outlet 54, 54', 54" of the respective container 44, 44', 44". The solenoid 52, 52', 52" is electrically coupled to the micro-processor 16 so as to facilitate automated formulation and dispensing of consumables, via the central computer 20, as discussed below in further detail.

The conveyance device 46 extends between the mixing chambers 44, 44', 44" and the trough 24 and can be formed as an auger conveyor having an auger shaft 54 with a helical flange 56 that rotates within a cylindrical casing 58 thereby forcing consumables to travel along the length of the cylindrical casing 58 from the mixing chamber 48 to the trough 24. One end of the cylindrical casing 58 is open to the mixing chamber 48 such that consumables are directed into the cylindrical casing 58 and subsequently forced to the opposite end of the cylindrical casing 58 by rotation of the auger shaft 54. The opposite end of the cylindrical casing 58 is open to the interior of the trough 24 such that when the auger shaft 54 rotates, the consumables are forced into the interior of the trough 24. The auger shaft 54 communicates with and is rotationally driven by an actuator 60, for example an electrical motor. Thus the consumables are forced through the cylindrical casing 58 to the trough 24 when electrical current is supplied to the actuator 60. In a similar arrangement, the consumption dispensing station 14 can be formed by liquid conduits 50, 50', 50" having one or more solenoid valves 52, 52', 52" located in the conduits 50, 50', 50" which can be electrically actuated to open thereby facilitating the flow of liquid consumables from the containers 44, 44', 44", through the conduits 50, 50', 50" and mixing chamber 48 and to the trough 24. It is to be appreciated that the manner by which the consumables are supplied to the trough 24 is generally not critical, so long as the amounts (mass, weight, volume) and thereby the proportions of consumables delivered to the interior of trough 24 can be controlled. That is to say, it is important that the conveyance device 46 has an actuator 60 or actuators that can be controlled such that the amount of consumables supplied to the trough 24 by way of the consumption dispensing station 14 can be controlled. The actuator 60 or actuators of the conveyance device 46 communicate, via the micro-processor 16 and the communication device 18A, 18B, with the central computer 20 which controls the actuator 60 or actuators such that the amounts and formulations of consumables conveyed to the trough 24 can be controlled based on a number of factors to be discussed below.

The measurement unit 8 functions as a means for measuring the partial weight of an animals 4 which is then used for calculating the full weight of the animals 4 as will be described below. The measurement unit 8 has front braces 62 that are connected to the front panel 26 and extend generally perpendicular relative to the front panel 26 in a direction opposite the consumption dispensing station 14. The front braces 62 support one or more load cells 64 which directly support the weight platform 66 and, as is conventional in the art, function as scales. The weighing device 12 further includes the weight platform 66 on which the animals 4 is to stand while at the measurement unit 8. According to the present invention, the weight platform 66 is supported by at least one load cell 64, e.g., the weight platform is supported by a centrally located load cell or by, a pair of opposed load cells or by a load cell supporting each corner of the weight platform. Due to this configuration, the weight supported on the weight platform 66 is focused on and completely supported by the respective load cells 64 for accurately determining the partial weight of the animal 4. As the use of load cells 64, for measuring weight, is generally known in the art, a further detailed discussion concerning the use of such load cells 64 will not be provided herein. An important feature of the load cells 64, according to the present invention, is that they should be configured so as to continually monitor and measure the partial weight of the animals 4 and transmit these weight measurements to the micro-processor 16 and the remote computer 20 for recordation and analysis thereof, as will be discussed below in further detail. The load cells 64 can be arranged in any manner with respect to the weight platform 66 as long as the partial weight of the animals 4 rests upon the load cells 64 for accurate measurements thereof.

The measurement unit 8 is arranged with respect to the consumption dispensing station 14 to measure the partial body weight of animals 4 while they consume the consumables provided in the trough 24. The measurement unit 8 is arranged, with respect to front panel 26 such that the neck guides 38, the vertical and horizontal neck bars 30, 32 position only one animal 4 on the weight platform 66 at a time as the animals 4 consumes the consumables. Due to the relative size of the weight platform 66 and the alignment of the vertical neck bars 30 and neck guides 38, the animals 4 must place its forelegs on the weight platform 66 and insert its head through the opening 28 in the front panel 26 to consume the consumables provided in the trough 24. This ensures that, while at the consumption dispensing station 14, both forelegs of the animals 4 are generally centered on the weight platform 66, and minimizes the extraneous forces, which can transfer to the load cells 64 when the animal 4 comes in contact with the measurement unit 8. Thus, only the vertical forces exerted by the animal's forelegs are measured by the measurement unit 8.

Preferably, the front braces 62 of the measurement unit 8 can be raised or lowered with respect to the base frame 22 of the consumption dispensing station 14 so as to adjust the height of the weight platform 64 from the ground. Alternatively the edge support posts 34 can be adjusted so as to lower or raise the weight platform 66 with respect to the ground. The weight platform 66 is supported by the front braces 62 as well as by the load cells 64 such that the weight platform 66 is positioned substantially parallel to but spaced from the ground by a distance between about 1 to 8 inches. The weight platform 66 is suspended above the ground due to the possibility of the build up of mud in the vicinity of the measurement unit 8. The weight platform 66 can be cantilevered with respect to the front panel 26 to enable cleaning of the area around and underneath the weight platform 66 with little obstruction. The load cells 64 of the weight platform 66 can communicate with the micro-processor 16 either wirelessly or by conventional cabling (not shown in detail). A further detailed discussion concerning the collection and subsequent transmission of the weight measurements, collected by the micro-processor 16, will be discussed below.

The micro-processor 16 is coupled so as to communicate with one or more receiving devices 10 which comprises an RFID antenna that is typically embedded, for example, in a rim of the trough 24 and/or one of the vertical and horizontal bars 30, 32 of the front panel 26. The actual location or placement of the RFID antenna 10, with respect to the associated trough 24 and the front panel 26, is generally not critical, as long as the RFID antenna 10 is positioned so as to receive only the unique signal of the RFID transmitter 6 located on the animal 4 which extends its head through the opening 28 in the front panel 26 in order to consume the consumables from the trough 24, and not receive the unique signal of the RFID transmitter 6 from any other animal 4, specifically any animals 4 located adjacent the trough 24. In a similar manner to the load cells 64, the RFID antenna 10 also communicates with the micro-processor 16 for providing current information concerning the unique signal of the RFID transmitter 6 of the animals 4 currently feeding at the trough 24.

To facilitate tracking of each animal 4 to be monitored in the grazing environment, each of the animals 4 carries a RFID transmitter 6 and each transmitter 6, and thus each animal 4, is provided with a unique signal or rather a unique identification code. The RFID transmitter 6 is located generally on the animals 4 in the vicinity of the neck or head, or in the ear. As a result of such configuration, as an animal 4 approaches one of the measurement units 8 and accesses a trough 24 by extending its head through the opening 26 formed in the front panel 26, the RFID transmitter 6 is brought into sufficiently close proximity with the RFID antenna 10. Once the RFID transmitter 6 is within the detection range of the RFID antenna 10, e.g., within a range of between 2 to 50 inches for example, the RFID antenna 10 receives the unique signal being transmitted by the respective RFID transmitter 6. As noted above, this unique signals includes unique codes for the RFID transmitters 6 which are associated with the animals 4 currently consuming from the trough 24 so that the highly automated system 2, of the present invention, is able to identify the animals 4 and appropriately adjust the amount and/or formulation of the consumables provided to the trough 24. Once the unique signal is received by the RFID antenna 10, it is transmitted to the micro-processor 16 such that the measured partial weight can be associated with that respective animal 4.

The micro-processor 16 is associated with and/or coupled to a communication device 18A, 18B. As discussed briefly above, the micro-processor 16 is arranged, in a conventional manner, to communicate with each one of the load cells 64 and the associated RFID antenna 10 so as to receive respective unique signals and weight measurements from each of those devices so that the micro-processor 16 is informed regarding the respective animals 4 located at the measurement unit 8. The micro-processor 16 can further include a data storage unit 68 for temporarily recording and storing the weight measurements and unique signals from the load cells 64 and the RFID antenna 10 as well as the corresponding time that this information is collected. It is also possible that the micro-processor 16, may not have any separate data storage unit other than perhaps an internal memory. In this case, the micro-processor 16 merely collects and then retransmits all of the collected weight measurements, unique signals and time information, collected from the load cells 64 and the associated RFID antenna 10, to the central computer 20 via the communication device 18A, 18B, e.g., by local, satellite, cellular and internet communication networks wireless transmission or via conventional cabling (not shown).

As briefly discussed above, in addition to weight measurements, unique signals and time information, the central computer receives and collects further measurements, data and information from a wide variety of other devices, sensors and sources. These other devices, sensors and sources as well as the further measurements, data and information that they transmit to the central computer will be discussed in more detail below, however, suffice it to say, the further measurements, data and information are associated with climate and environmental data sources, geospatial data, grazing-land information, operational information regarding measurement units, equipment, animal, plant, and land assets, a variety of reference statistics, and specific animal information, etc. Upon receiving these further measurements, data and information, the central computer uses statistical methods, mathematical formulas, and algorithms to estimate, calculate, predict, monitor, evaluate, store and reevaluate animal, plant, soil, environment, operation and industry values, metrics, parameters and interactions with degrees of confidence. As one example, from the further measurements, data and information, the central computer determines an optimal amount and formulation of consumables to deliver to the specific animal currently present at the measurement unit so as to promote animal health, growth and welfare and reduce animal stress and environmental impact of the animal. In operation, the central computer 20 uses the weight measurements, unique signals and time information and further measurements, data and information to determine appropriate control signals which are then transmitted by the central computer 20, via the communication device 18A, 18B, to the actuators 52, 52', 52" and 60 generally associated with the consumption dispensing station 14 and specifically the conveyance device 46. As discussed above, appropriate signals can be sent to the actuators 52, 52', 52", e.g., solenoids, electrical motors and solenoid valves that are arranged, with respect to a path of conveyance, between the plurality of containers 44, 44', 44" and the mixing chamber 48, as well as to the actuator 60 associated with the conveyance device 46. According to the appropriate control signals received by one or more of these actuators 52, 52', 52" and 60, the amounts (mass, weight, volume) and thereby the proportions of consumables supplied to the trough 24 by way of the consumption dispensing station 14 are automatically controlled by the central computer 20.

A solar panel 70 can be used to provide power to the highly automated system 2 if a conventional power source is not available. It is to be noted that the highly automated system 2 can be configured so as to be semi-portable. That is to say, the highly automated system 2 can be lifted by the lug rings 72 (FIG. 2) and may be moved using a front-end loader or, if supplied with wheels, wheeled by an attached trailer. The mobility of the highly automated system 2 is beneficial in grazing animal production environments, such as in grazing-land that is divided into different paddocks. In this type of environment, the highly automated system 2 can be moved between different paddocks based on known land use and grazing management techniques.

The highly automated system 2 can also be utilized with different feed management strategies. One strategy for feeding animals is known as "limit" feeding. This strategy includes limiting the amount of feed that is provided to an animal over the course of a specific time period. With this strategy, even after consuming all of the consumables supplied to the trough, the animals do not get the sensation of being "full", that is to say, their hunger is not fully satisfied. In this condition the animals commonly seek consumables away from the highly automated system 2, including forcibly accessing adjacent pastures. Generally, animals are restricted to grazing in specific pastures with electric fences. Solar powered electric fences are relatively easy to install and can readily be moved by hand when relocation of the animals to a different pasture is desired. This type of land management can be accomplished with the highly automated system 2, since it can be used to "train" animals to come to and stay relatively near the dispensing station 14. It has been found that "trained" animals follow the highly automated system 2 when it is moved from one pasture to another. To train the animals, the consumables are formulated so as to be very attractive to eat, such as by adding sugar to instead of salt. During "training" the highly automated system 2 supplies the consumption dispensing station 14 with the "sweetened" consumables at relatively regular intervals such that the animals remain in the relative vicinity of the highly automated system 2. It is beneficial for the highly automated system 2 to include a signaling assembly 73 (FIGS. 3 and 5) which notifies the animals that the "sweetened" consumables are available. The signaling assembly 73 can include one or more lights 75, beepers and/or horns 77, for example. The signaling assembly 73 communicates with the central computer 20 and a power source and is attached to the highly automated system 2 in an easily visible location such as atop the front panel 26. The signaling assembly 73 is activated by the central computer 20 at relatively regular time intervals so as to alert the animals of the availability of "sweetened" consumables. The time intervals at which the signaling assembly 73 is activated can be adjusted so as to control the distance by which the animals will graze away from the highly automated system 2. It has been found that "trained" animals follow the highly automated device 2 when it is moved from one pasture to another.

The central computer 20 can transmit control signals to an animal marking device 74 which when activated visibly marks animals 4, that may require intervention, by spraying a single color or combination of colors and/or applying a pest control substance on the animal 4 while the animal 4 is consuming substances. This enables visible identification and/or sorting of animals 4 by behavior characteristics, group adaptation or lack thereof, weight and growth or lack thereof, or consumption patterns. This type of visual marking will also enable specific types of animals 4 such as aggressive animals 4 to be removed from contact with the other animals 4. As animal marking systems 74 are generally known, the same will not be discussed in further detail.

Figure 2:
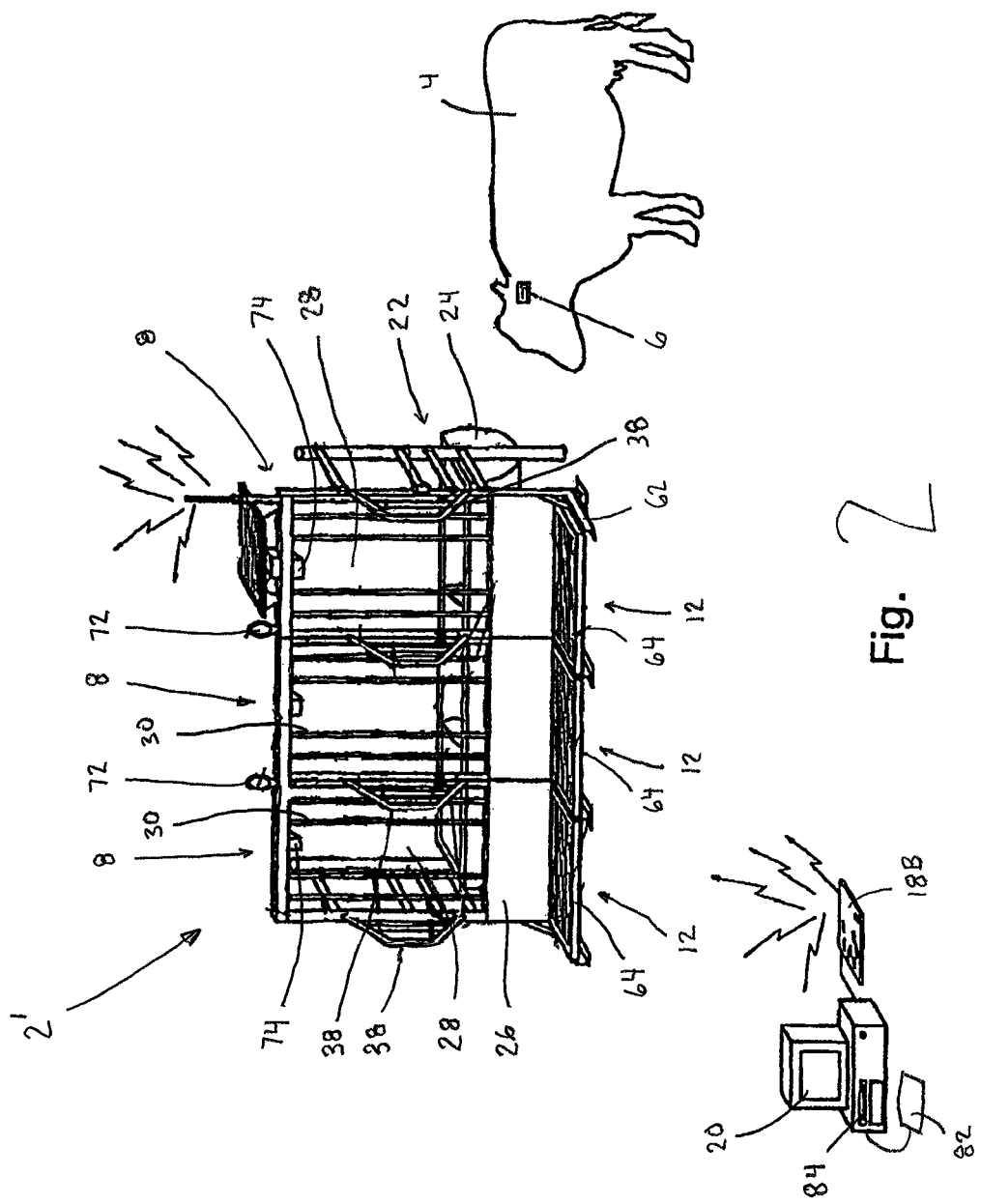
FIG. 2 is a perspective view of the system where more than one measurement unit identifies, measures, monitors, manages and controls a grazing environment and animals in accordance with the teachings of the present invention.

A second embodiment of the highly automated system 2 is shown in FIGS. 2 and 5. As this embodiment is quite similar to the embodiment illustrated in FIGS. 1 and 4, the following description will focus on the distinctions of this embodiment in comparison to the previously described embodiment. The second embodiment comprises a base frame 22 which supports a plurality of measurement units 8 which are attached, joined or bolted together to form an expanded highly automated system 2' for identifying, measuring, managing and controlling of the consumption behavior, substance intake, weight and growth, reproduction movement and harvest of individual animals 4 in grazing environments at the same time. This configuration enables multiple animals 4 to consume consumables and be weighed at the same time. It is to be appreciated that each of the measurement units 4 can be formed individually and thereafter coupled to each other in a mechanically appropriate manner, for example by welding the base frames and front panels together, or by connecting the base frames and front panels together by nuts and bolts, screws, and coupling brackets. The highly automated system 2' with multiple measurement units 4 can also be formed having a single elongate base frame that can support a number of individual troughs 24 and a front panel having a corresponding number of sets of neck guides 38 and openings 28. In such a highly automated system 2', the plurality of troughs 24 are supported on the base frame so that the troughs 24 are arranged in series closely adjacent one another.

In the second embodiment, it should be appreciated that the actual location or placement of the RFID antenna 10, with respect to the associated feed trough 24 and the front panel 26, is generally not critical, as long as the RFID antenna 10 is positioned so as to receive the unique identification information code signal of only the animal 4 which extends its head through the corresponding opening 28 in the front panel 26 in order to consume the consumables from the associated trough 24, and not receive the unique identification information code signals from any other animal 4, specifically an animal 4 at an adjacent trough 24.

Each consumption dispensing station 14 in the second embodiment can comprise a conveyance device 46 and containers 44, 44' that are independent of the consumption dispensing station 14 of other measurement units 8. The arrangement of measurement unit 4 comprising its own consumption dispensing station 14 independent of other measurement units 4 is generally described above and as such no further discussion thereof is believed to be necessary. It is possible, in an alterative arrangement of the second embodiment, that each of the conveyance devices 46' of the different measurement units 8' convey consumables from a set of common containers 45, 45' or even a common mixing chamber 48' thereby reducing the number of containers and mixing chambers and the costs associate therewith. With this arrangement a single set of containers 45, 45' and a single mixing chamber 48 can supply consumables to two or more of troughs 24', 24'.

In the second embodiment comprising a plurality of consumption dispensing stations 14, each consumption dispensing station 14 is associated with a respective weighing device 12 such that only one animal 4 can be weighed at a time at each corresponding consumption dispensing station 14. It is important that the weighing platforms 66 of the different measurement units 8, 8' do not contact one another as such contact would interfere with determination of accurate partial weight measurements of the individual animals 4. It should be understood that each of the weighing platforms 66 is supported by load cells 64 that are only associated with that single measurement unit 8, 8'. That is to say, the one or more load cells 64 that support and measure the partial weight of one animal 4 at one weighing device 12 can not be used to support and measure the partial weight of another animal 4 at an adjacent weighing device 12 for example.

In the second embodiment, the load cells 64 associated with the different weight platforms 66 communicate with a single micro-processor 16 either wirelessly or by conventional cabling (not shown in detail) so as to measure and transmit the partial weights of the respective animals 4 to the micro-processor 16. Although it is possible that each of the measurement units 8, 8' of the second embodiment comprises its own micro-processor 16, it is preferable that load cells 64 of all of the measurement units 8, 8' communicate with a single common micro-processor 16.

As previously noted, the central computer communicates with a wide variety of other devices, sensors and sources which transmit further measurements, data and information to the central computer. With respect to these other devices, it should be understood that one of more of the same devices can be utilized for multiple measurement units depending on the type of measurements, data and information that specific device measures, detects or gathers. For example, if the amount of rainfall was one of the measurements being monitored, each measurement unit 8, 8' of the enhanced highly automated system 2' would not be required for each of the plurality of measurement units 8, 8'. The other devices, sensors and sources as well as the measurements, data and information associated therewith will now be discussed below A location transmitting device 76 (FIG. 4) can be affixed to the highly automated system 2 or to the animals 4 so as to communicate with the central computer 20. The location transmitting device 76 can provide the central computer 20 with reference information related to geospatial data which is utilized by the central computer 20 to determine the geographical location of the measurement units 8 and movement of the animals 4 on the grazing-land and/or in the paddocks.

A dimension measuring device 78 can be incorporated into each of the measurement units 8 so as to detect and measure the dimensions of the animal 4 and/or forage material in the pasture area surrounding the highly automated system 2.

A variety of environmental sensors 80 are incorporated into the highly automated system 2 which measure environmental conditions and transmit the associated sensor measurements to the central computer 20. The environmental sensors 80 can measure at least one of ambient temperature, daily and/or weekly precipitation amounts, current barometric pressure, wind speed, wind direction, humidity, atmospheric composition, insolation, soil moisture, measurements indicative of the amount of sunlight, as well as other environmental information.

An input device 82 (FIG. 1) can input data and information into at least one of the RFID transmitters 6 and/or central computer 20. The data and information that can be input by way of the input devices 82, can relate to specific pastures, paddocks, one animal 4 or all of the animals 4 combined and can include at least one of animal birth date, animal purchase price, animal breed and genetic pedigree, animal genotype, animal body condition, animal chute weights, animal frame size, animal harvest yield, quality and sale price, supplement type, quantity administered and cost, medication type, quantity administered and cost, pasture size, forage type, forage mass, forage chemical properties, fertilizer application, herbicide treatment, soil physical properties.

The central computer can utilize devices which can measure, detect, determine and obtain at least one of time, date, growth, environmental conditions and other relevant measurements and reference statistics so as to determine the health status of individual animals and/or the availability of forage and determines the requirement for nutrients, vitamins, minerals, trace minerals, salt and/or medicated products and activates the consumption dispensing stations to dispense a specific amount of a supplemental mineral nutrients, vitamins, minerals, trace minerals, salt, pest control and/or medicated products to be ingested by each specific animal. Such measurement, data and information can be utilized by the central computer to determine and/or predict the optimum time for estrous synchronization and activate the consumption dispensing station to dispense a specific amount of compound to be ingested by a specific animal so as to promote breeding programs. Such information can also be considered for grazing environment management purposes such as to determine where to place and move fencing.

The following example illustrates the function and operation of the highly automated system for monitoring and managing individual animals in a grazing production environment. As generally described above, when an animal approaches a measurement unit so as to obtain supplements from the trough, the highly automated system ascertains the identity of that specific animal by means of the RFID transmitter attached to the animal and the RFID antenna connected to the system. With the identity of the specific animal known, among other things, the system detects and records the partial body weight and from that calculates the total body weight of that specific animal. By tracking different physical features and patterns of behavior of that specific animal, the system can detect or determine the health status of that particular animal. Based on the specific health status as well as a number of other factors as described above, the system can customize and provide that specific animal with different formulations and/or quantities of supplements. The formulation and quantity of the supplements provided to that specific animal can be customized according, not only to the health status of that particular animal, but can also depend on one or more of a host of other factors and considerations. For example, environmental conditions such as the amount of precipitation can be considered when customizing the formulation or quantity of supplements. Either too little or too much precipitation can cause the nutritional quality of grass to decrease which can then result in a deficiency of nutrients in animals. Thus if the highly automated system detects that too much or too little precipitation has fallen on the grazing-land over a given period of time, then the formulation and/or quantity of the supplements can be adjusted to offset the reduced nutritional quality of the forage, that is to say, the supplements can be formulated so as to have a higher nutritional value.

In the above example, another factor that may be considered when adjusting the formulation of the supplement, meaning the type and/or quantity of nutrients to be provided to that specific animal can also be the age of the animal. For example given the adverse amount of precipitation over the given period of time, although it may be recognized that a supplement having a higher nutritional value is needed, the types of nutrients most beneficial for an older animal are likely to be different than the types of nutrients most beneficial for an adolescent animal. As another example, if no precipitation has fallen on the grazing-land for an extended period of time, the animal may be deficient of protein. In this case, when the highly automated system recognizes that no precipitation has fallen, and based on reduced intake and/or growth rate the animal, as determined by tracking the animals weight, the formulation and/or quantity of the supplement may be adjusted to have a small or large increase of protein.

With either of the above examples, the formulation and/or the amount of supplement to be provided to the animal can further be dependent on the frequency at which the animal approaches the highly automated system. As would be expected, a first animal that, on average, approaches the highly automated system many times a day would be provided with a formulation and/or amount of supplement having a lower nutritional value than a second animal that, on average, approaches the highly automated system a lower number of times a day so as to avoid over-supplementation of the first animal.

The central computer 20 has a computer readable storage medium 84 in communication with a processor which uses above discussed relevant measurements, data, information and statistics calculated on a time interval basis referenced to previous time interval basis to monitor and predict animal growth, efficiency, productivity, performance and/or reproduction economic animal breeding value, forage mass, forage properties, predict forage growth, supplementation, and other and reference statistics to determine at least one of the optimum stocking density, carrying capacity, grazing protocol, time to move the cattle from one grazing location to another, time to market cattle, and at least one of these determinants is used to calculate the economic value per unit of measurement for each grazing location. The computer uses relevant measurements, data, information and statistics: to estimate a carbon offset, a greenhouse gas or conservation value for an animal, and/or a location and/or an operation; to monitor, maintain and inventory measurement units, equipment, animal, plant, and land assets; to monitor measurement units, equipment, animal, plant, and land assets providing an audit, quality, security and verification record to participants in alliance natural, organic, branded and quality programs.

The computer readable storage medium 84 as described herein can be a data storage device, or unit such as a magnetic disk, magneto-optical disk, an optical disk, or a flash drive. Further, it will be appreciated that the term "memory" herein is intended to include various types of suitable data storage media, whether permanent or temporary, such as transitory electronic memories, non-transitory computer-readable medium and/or computer-writable medium.

It will be appreciated from the above that the invention may be implemented as computer software, which may be supplied on the computer readable storage medium or via a transmission medium such as a local-area network or a wide-area network, such as the Internet. It is to be further understood that, because some of the constituent system components and method steps depicted in the accompanying Figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

While various embodiments of the present invention have been described in detail, it is apparent that various modifications and alterations of those embodiments will occur to and be readily apparent to those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having," and variations thereof herein, is meant to encompass the items listed thereafter and equivalents thereof as well as additional items while only the terms "consisting of" and "consisting only of" are to be construed in a limitative sense.

We claim:

1. A highly automated system of measuring and managing individual animals in a grazing production environment comprising:
   a transmitter is one of attached, implanted and ingested on or by a particular animal which identifies the particular animal by a unique signal,
   a measurement unit on which measurement devices are mounted the measurement unit comprising:
      a receiving device that receives the unique signal from the transmitter,
      a weighing device that measures a partial body weight of the animal,
      a consumption dispensing station that supplies substances to the specific animals,
   a microprocessor that receives, processes and transmits and controls signals from devices attached to the measurement unit,
   a communication device that receives and transmits signals from the measurement unit to other measurement units, and at least one of locally and remotely positioned computers via at least one of local, satellite, cellular and Internet communication networks,
   the computer that is local or remotely situated and receives the signals, and which also collects measurements from other devices and uses statistical methods, mathematical formulas, and algorithms to estimate, calculate, predict, monitor, evaluate, store and reevaluate animal, plant, soil, environment, operation and industry values, metrics, parameters and interactions with degrees of confidence, and
   the consumption dispensing station being variably actuable by the computer to supply variable formulations and amounts of substances to the particular animal currently located at the measurement unit based on the values, the metrics, the parameters and the interactions.

2. The system according to claim 1, wherein a plurality of measurement units are distributed across multiple grazing locations.

3. The system according to claim 1, wherein the measurement unit is portable.

4. The system according to claim 1, wherein a spraying and marking device is incorporated into the highly automated system, the spraying and marking device at least one of visually colors the particular animal and applies pest control substances to the particular animal when consuming substances.

5. The system according to claim 1, further comprising a measurement device that measures at least one of dimensions of the animal and dimensions of forage material in a pasture area surrounding the highly automated system, the consumption dispensing station being controllably actuated to adjust at least one of an amount and a formulation of the substances supplied to the particular animal based on at least one of the dimensions of the animal and the dimensions of forage material in the pasture area.

6. The system according to claim 1, wherein sensors are incorporated into the highly automated system, the sensors measure at least one of:
   ambient temperature,
   precipitation,
   wind speed,
   humidity,
   atmospheric composition,
   insolation,
   soil moisture,
   and the measurements are referenced in the computer to data that is available from other climate and environmental data sources.

7. The system according to claim 1, wherein at least one of
   animal birth date,
   animal purchase price,
   animal breed and genetic pedigree,
   animal genotype,
   animal body condition,
   animal chute weights
   animal frame size
   animal harvest yield, quality and sale price
   supplement type, quantity administered and cost,
   medication type, quantity administered and cost,
   pasture size,
   forage type,
   forage mass,
   forage chemical properties,
   fertilizer application,
   herbicide treatment,
   soil physical properties,
   are input into the computer.

8. The system according to claim 1, wherein a transmitting device is affixed to the measurement unit and provides a geographical location of the measurement unit.

9. The system according to claim 1, wherein a transmitting device is affixed to the measurement unit, and at least one of:
   a location transmitting device is affixed to the animal,
   a dimension measurement device, and
   reference information to geospatial data from other sources are calculated in the computer to determine a geographical location and movement of the animal.

10. The system according to claim 1, wherein the computer being configured to determine and monitor at least one of a health status of the individual animals and an availability of forage based on at least one of time, date, growth, weight, behavior, environmental conditions and other relevant measurements and reference statistics.

11. The system according to claim 1 wherein the computer using at least one of time, date, growth, environmental conditions and other relevant measurements and reference statistics determines at least one of a health status of individual animals and an availability of forage and determines the requirements of the individual animals for at least one of nutrients, vitamins, minerals, trace minerals, salt and medicated products, the consumption dispensing station being controllably actuated by the computer to dispense a specific amount of at least one of a supplemental mineral nutrients, vitamins, minerals, trace minerals, salt, pest control and medicated products to be ingested by a specific animal based on the determined requirements of the specific animal.

12. The system according to claim 1 wherein the computer using at least one of time, date, age, weight, animal behavior, environmental conditions and other relevant measurement and reference statistics at least one of determines and predicts the optimum time for estrous synchronization, the consumption dispensing station controllably activated to dispense a specific amount of compound to be ingested by a specific animal, based on the at least one of the determined and the predicted optimum time for estrous synchronization, the compound promoting breeding of the specific animal.

13. The system according to claim 1 wherein the computer uses at least one of animal type, age, weight, predicted animal growth, forage mass, forage properties, predicted forage growth, supplementation, and other relevant measurements and reference statistics to determine at least one of the optimum
   stocking density,
   carrying capacity,
   grazing protocol
   time to move the animals from one grazing location to another,
   time to market the animals,
and at least one of these determinants is used to calculate an economic value per unit of measurement for each grazing location.

14. The system according to claim 1 wherein the computer uses at least one of animal type, age, weight, predicted animal growth, forage mass, forage properties, predicted forage growth, supplementation, and other relevant measurements and reference statistics to determine where to place and move fencing.

15. The system according to claim 1 wherein the computer uses collected measurements and statistics calculated on a time interval basis referenced to previous time interval basis to monitor and predict future measurement unit, animal, forage and whole system status.

16. The system according to claim 1 wherein the computer uses relevant measurements and reference statistics to at least one of estimate and predict at least one of growth, efficiency, productivity, performance and reproduction economic animal breeding value.

17. The system according to claim 1 wherein the computer uses relevant measurements and reference statistics to estimate a carbon offset, a greenhouse gas or conservation value for at least one of an animal, a location and an operation.

18. The system according to claim 1 wherein the computer uses relevant measurements and reference statistics acquired to monitor, maintain and inventory measurement units, equipment, animal, plant, and land assets.

19. The system according to claim 1 wherein the computer uses relevant measurements and reference statistics to monitor measurement units, equipment, animal, plant, and land assets providing an audit, quality, security and verification record to participants in alliance natural, organic, branded and quality programs.

20. The system according to claim 1 wherein the computer supplies the substance at various time intervals and amounts thereby the computer controls how far the animals will graze away from the consumption dispensing station.

21. A highly automated system of measuring and managing a plurality of individual animals in a grazing production environment, the highly automated system comprising:
   a transmitter being connected to each of the individual animals, each of the transmitters conveying a unique signal which identifies the individual animal associated with that transmitter;
   a measurement unit having a plurality of measurement devices mounted thereon, the measurement unit having:
      a weighing device that measures a partial body weight of a specific animal that is currently positioned on the measurement unit,
      a receiving device that receives the unique signal from the transmitter which identifies the specific animal associated with that transmitter and currently positioned on the measurement unit, and
      a consumption dispensing station having at least one container, which accommodates a supply of consumables, and a conveyance device which conveys the consumables from the container to a trough that is adjacent the weighing device;
   a microprocessor being attached to the measurement unit receiving, processing and transmitting a partial body weight measurement and the unique signal from the weighing and the receiving devices, respectively;
   a communication device receiving and transmitting additional signals of other measurement devices, the partial body weight measurement and the unique signal from the measurement unit to a computer via at least one of local, satellite, cellular and Internet communication networks;
   the computer receiving the additional signals, the partial body weight measurement and the unique signal, and determining therefrom, a condition of at least one of the specific animal and the grazing production environment; and
   the consumption dispensing station being variably actuatable by control signals transmitted by the computer to supply at least one of a variable formulation and a variable amount of consumables to the specific animal based on the determined condition of the at least one of the specific animal and the grazing production environment.

* * * * *